United States Patent
Gilevich

(10) Patent No.: US 7,234,510 B1
(45) Date of Patent: Jun. 26, 2007

(54) X-RAY FOOD INSPECTION CONSOLE SUPPORT AND COOLING SYSTEM

(75) Inventor: Alexander I. Gilevich, Sunnyvale, CA (US)

(73) Assignee: InspX, LLC, Fremont, CA (US)

( * ) Notice: Subject to any disclaimer, the term of this patent is extended or adjusted under 35 U.S.C. 154(b) by 295 days.

(21) Appl. No.: 10/606,078

(22) Filed: Jun. 26, 2003

(51) Int. Cl.
*H05K 7/20* (2006.01)

(52) U.S. Cl. .............. 165/47; 165/104.33; 165/104.34; 454/184; 361/695; 361/690

(58) Field of Classification Search ................ 165/47, 165/104.33, 104.34; 454/184; 62/186; 361/695, 361/690
See application file for complete search history.

(56) References Cited

U.S. PATENT DOCUMENTS

| | | | |
|---|---|---|---|
| 4,887,437 A * | 12/1989 | Fenton et al. ............... | 62/186 |
| 6,353,532 B1 * | 3/2002 | Landrum et al. ........... | 361/683 |
| 6,506,111 B2 * | 1/2003 | Sharp et al. ................. | 454/184 |
| 6,944,020 B2 * | 9/2005 | Wintersteen et al. ....... | 361/687 |

| | | | |
|---|---|---|---|
| 2004/0180620 A1 * | 9/2004 | Sharp et al. ............... | 454/184 |

FOREIGN PATENT DOCUMENTS

JP 03250698 A * 11/1991

* cited by examiner

*Primary Examiner*—John K. Ford
(74) *Attorney, Agent, or Firm*—J. E. McTaggart

(57) ABSTRACT

A closed forced air system cools the electronic circuitry in a control console of an x-ray inspection station directed to food products in containers. A U-shaped tubular duct located beneath the console enclosure has both upwardly-directed ends attached to the bottom panel of the enclosure with openings provided for airflow communication, thus creating a closed loop air passageway. A pair of electric fans are installed at the upper ends of the U-shaped duct in manner to circulate air flow through the loop. Air in the enclosure, warmed by the electronic control circuitry, is drawn by one fan down into one arm of the U. The duct acts as a heat dissipater, and cool air at the opposite arm of the U is drawn by the other fan back up into the enclosure. The bottom of the U-shaped duct is attached to a front region of a support platform at the floor level and thus the arms of the U serve as a front pair of supports. A straight tubular support strut, extending from the enclosure down to a rear portion of the platform as a rear support, may serve as a wiring conduit.

3 Claims, 2 Drawing Sheets

US 7,234,510 B1

X-RAY FOOD INSPECTION CONSOLE SUPPORT AND COOLING SYSTEM

FIELD OF THE INVENTION

The present invention relates to the field of x-ray inspection of materials in containers, and more particularly to a combined support structure and closed air cooling system for a control console of an x-ray station that automatically inspects containers of food and beverages moving along a conveyor.

BACKGROUND OF THE INVENTION

X-rays have been used for inspection purposes for many years especially for the ability to detect impurities with higher density than the substance under test. Typically a shielded head-end unit including an x-ray source and an x-ray sensor is deployed onto a production line conveyor along which containers of food and beverages are moved through the head-end unit where they are automatically inspected in sequence.

Typically the x-ray source, sensor and conveyor driving mechanism are controlled from a control console which is located nearby in a separate enclosure and which usually includes a microprocessor along with electronic control and logic circuitry for administering the inspection program. This equipment consumes substantial electrical power and thus produces corresponding heat, which if not removed effectively, can expose the electronic circuitry to excessively high temperature, risking loss of reliability or even failure and shutdown due to thermal stress.

Many types of modern electronic equipment such as desktop computers rely on one or more air fans to remove excessive heat from components that are heat-producing and/or temperature-sensitive. Such cooling systems are typically "open" systems that draw air in from the surrounding room environment. Unfortunately, particularly in industrial environments, the air often contains dust, dirt and/or other contaminants to the extent that a filter is required on each fan. Even with a filter, there can be frequent need for maintenance which can include disassembly of the equipment to at least clean or replace the filter, and often it becomes necessary to clean the internal components, and particularly the fan blades which can become loaded with extraneous material and rendered ineffective.

Typical available electronic control equipment is packaged in enclosures of either desktop or rack-mounted type; however the production line environment often does not have suitable desktop space available in the desired location, and rack-mounting may be considered unacceptable due to cost or other reasons.

DISCUSSION OF KNOWN ART

U.S. Pat. No. 4,534,381 to Brown for a COOLING SYSTEM discloses a closed loop air passageway with air circulated by a single fan, utilized to cool a refrigeration system evaporator located in an enclosure which is incorporated into the loop.

U.S. Pat. No. 5,513,500 to Fischer et al for a SYSTEM FOR COOLING FOOD IN AN AIRPLANE discloses a closed loop air passageway including a fan and a heat exchanger, utilized to cool food located-multiple enclosures, i.e. on board galleys.

The two foregoing patents are examples of "closed" air circulation systems wherein air is confined with the passageways of a closed loop around which the captive air is typically circulated by a fan. Thus captivated within the closed system, the circulating air remains free from contaminants and impurities that may be present in the environmental air.

OBJECTS OF THE INVENTION

It is a primary object of the present invention to provide an effective cooling system for the electronic circuitry in a control console of an x-ray system addressed to inspection of food and beverage materials in containers moving along a conveyor.

It a further object to provide a floor support structure for holding the control console in a desired location near the x-ray head end portion.

It is a still further object to integrate the cooling system and the support structure through dual-purpose utilization.

SUMMARY OF THE INVENTION

The abovementioned objects have been met by the present invention of a closed air cooling system for the electronic circuitry in a control console of an x-ray inspection station directed to food products in containers. A U-shaped tubular duct located beneath the console enclosure has both upwardly-directed arm ends attached to the bottom panel of the enclosure with openings provided for airflow communication, thus creating a closed loop air passageway. A pair of electric fans are installed at the upper ends of arms of the U-shaped duct in manner to circulate air flow through the loop. Air in the enclosure, warmed by the electronic control circuitry, is drawn by one fan down into one arm of the U. The duct acts as a heat dissipater, and cool air at the opposite arm of the U is drawn by the other fan back up into the enclosure. The bottom of the U-shaped duct is attached to a front region of a support platform at the floor level and thus the arms of the U serve as a front pair of supports. A straight tubular support strut, extending from the enclosure down to a rear portion of the base platform as a rear support, may serve as a wiring conduit.

BRIEF DESCRIPTION OF THE DRAWINGS

The above and further objects, features and advantages of the present invention will be more fully understood from the following description taken with the accompanying drawings in which.

DETAILED DESCRIPTION

Figure 1:
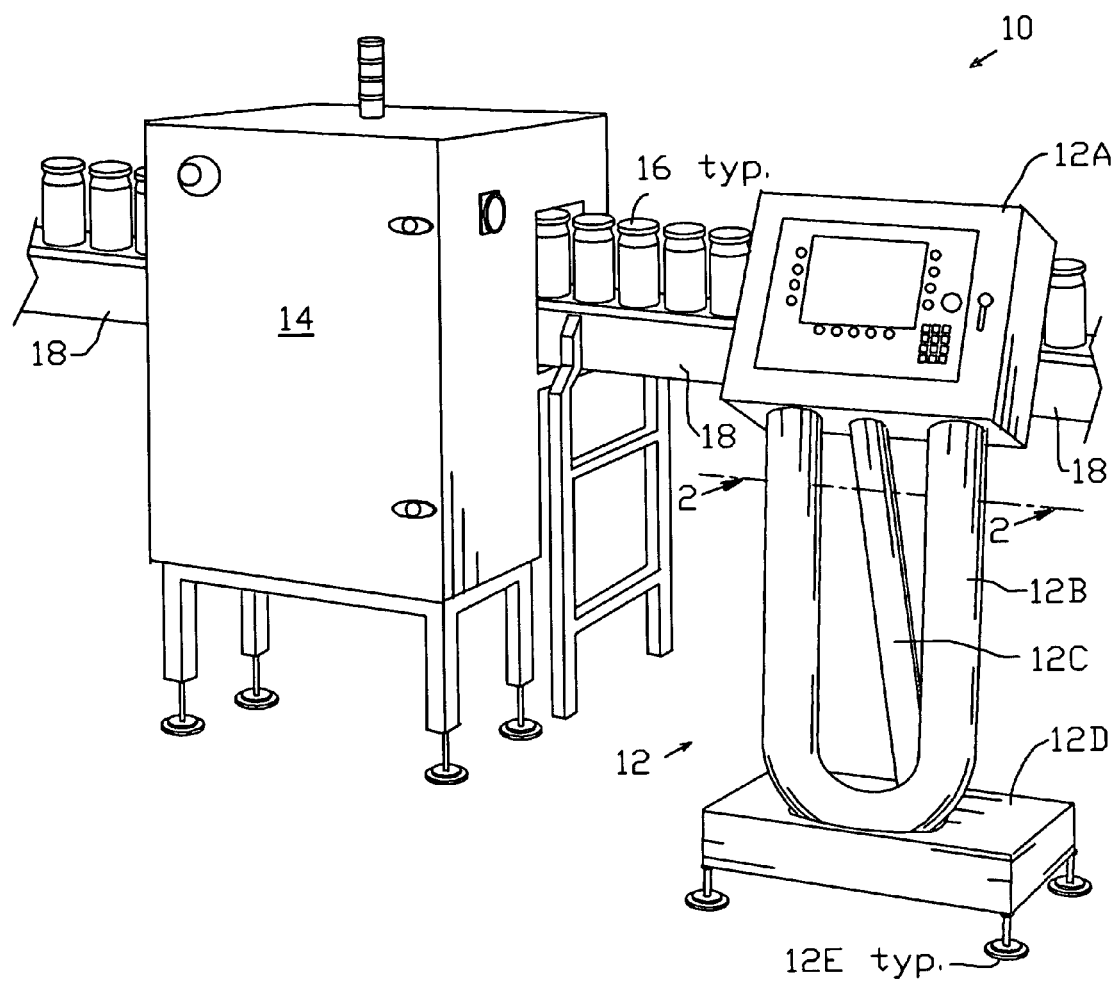
FIG. 1 is a perspective view of an x-ray inspection station including a control console that is cooled and supported in accordance with the present invention.

FIG. 1, a perspective view of an x-ray inspection station 10 of the present invention, shows a control console unit 12 which controls an x-ray "head end" unit in enclosure 14 through which food/beverage containers 16 are moved along a conveyor 18 for x-ray inspection. Both the movement of containers 16 along conveyor 18 and the sequential activation of x-ray apparatus in enclosure 14 are controlled by a microprocessor and associated electronic control circuitry in enclosure 12A, which typically provides on its front panel a readout display, an alpha-numeric keypad and a number of pushbutton user controls.

Attached onto the bottom panel of enclosure 12A and in airflow communication with its interior are the open upper ends of the two arms of a U-shaped tubular heat-dissipating duct 12B, which is typically four inches in diameter, and which, along with a straight tubular support strut 12C, typically two inches in diameter, is fastened at the lower end to a generally rectangular base platform 12D, supported on the floor by four screw leveling feet 12E. Preferably enclosure 12A, U-shaped duct 12B, straight strut 12C and base platform 12E are all made from stainless steel and fastened together by welding or other appropriate structural fastenings.

The electronic circuitry in enclosure 12A is connected to the "head end" unit in enclosure 14 by an electrical cable (not shown), which may be directed through tubular strut 12C, serving as a conduit.

The enclosure 12A is tilted backward somewhat, as shown, for ease of observation and operation.

Figure 2:
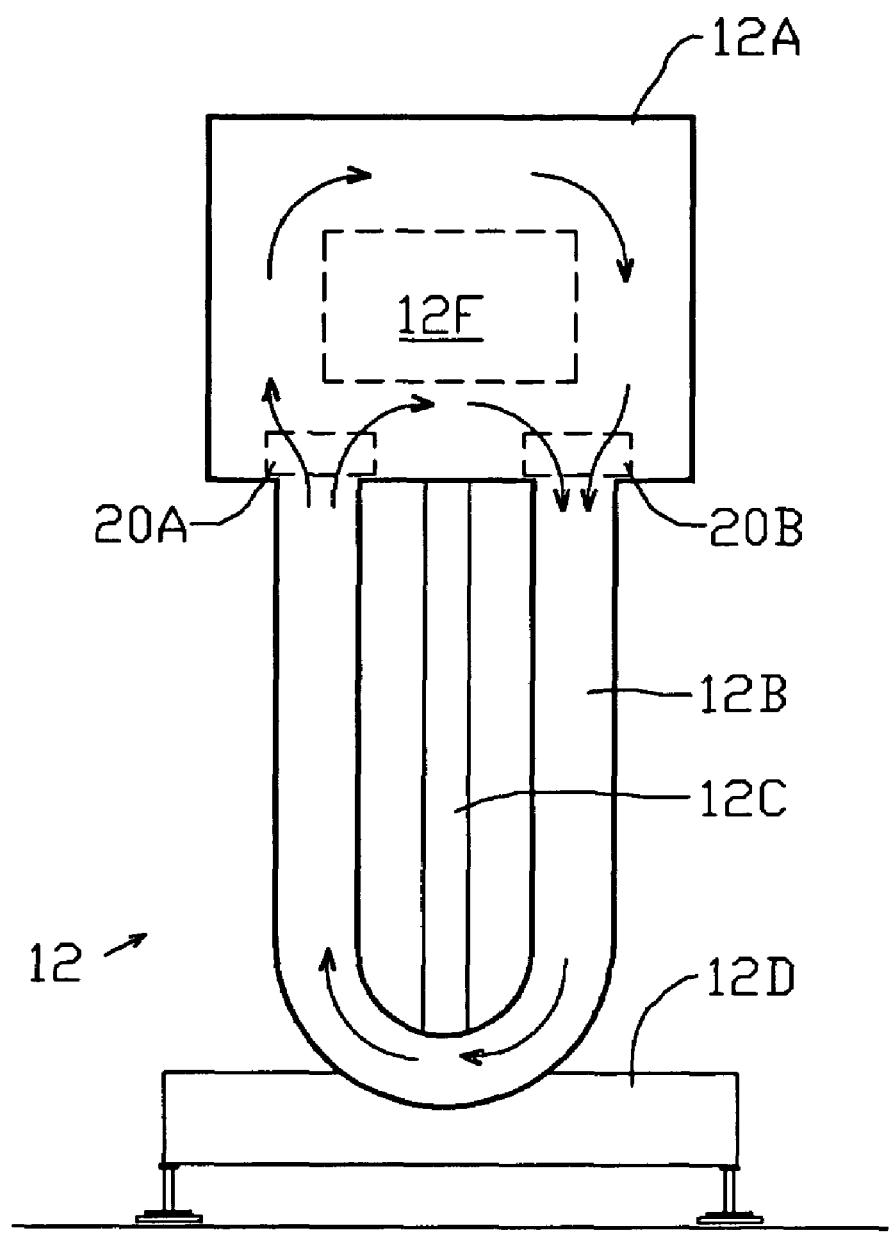
FIG. 2 is a cross-sectional elevational view of the console unit of FIG. 1 taken through axis 2-2 showing the locations of the two fans and indicating a clockwise air flow circulation.

FIG. 2, a cross-sectional representation and front elevational view of inspection station 12 taken through axis 2-2 of FIG. 1, shows in broken outline the general location of the electronic module 12F centered in enclosure 12A, and two electric fans 20A and 20B at the corresponding openings at the top ends of the U-shape duct 12B. The two fans are of a popular type, e.g. as marketed under registered trademarks such as Whisper and Muffin, and are oriented oppositely so as to cause airflow circulation in the clockwise direction as indicated by the arrows. Warm air from enclosure 12A is made to flow downwardly into the right hand arm of duct 12B, whose large surface area functions as a heat dissipater to bring the air temperature down to near room temperature, returning the cooled air upwardly from the left hand arm of duct 12B, back into enclosure 12A where it flows past module 12F to continuously remove heat therefrom.

Enclosure 12A and U-shaped duct 12B are generally made to be as airtight as possible to minimize intake of environmental air, so that the captive recirculating air remains clean for long periods of continuous operation, thus minimizing maintenance cost for cleaning and replacing filters, while the low operating temperature maintained enhances the reliability of the electronic circuitry.

While the foregoing description represents an illustrative and preferred embodiment in which the invention has been successfully practiced, there are alternative manners in which it may be practiced.

As an alternative to the U-shaped duct shown, two straight ducts corresponding to the two arms of the U could be directed into the base platform 12B, which would be fully enclosed to act as a series element in the airflow passageway.

The clockwise air flow pattern shown in FIG. 2 could be reversed by reversing the direction of both fans 20A and 20B. Normally there would be little if any difference unless the module 12E is subject to unusual asymmetrical thermal issues that need to be considered.

The invention could be practiced with just one fan at one of the duct ends, oriented for airflow in either direction. The choice of ends and flow direction could be determined empirically by temperature measurements.

For controllers of relatively low power rating, the basic principles of the invention could extended even further to include operation without a fan, i.e. with air circulation depending on gravity only, in the manner of gravity hot air residential heating. This would be best implemented by a C shaped duct drawing off warm air through the top panel of the enclosure and returning the cooled air into its bottom panel. Structurally, the support function would be better served by a parallel pair of such ducts located side-by-side, e.g. with their front portions corresponding to the arms of the U-shaped duct 12B, FIGS. 1 & 2.

The invention may be embodied and practiced in other specific forms without departing from the spirit and essential characteristics thereof. The present embodiments are therefore to be considered in all respects as illustrative and not restrictive, the scope of the invention being indicated by the appended claims rather than by the foregoing description; and all variations, substitutions and changes which come within the meaning and range of equivalency of the claims are therefore intended to be embraced therein.

What is claimed is:

1. A combined support structure and cooling duct system providing physical support and cooling of electronic circuitry in a control console of a type suitable for use in conjunction with an x-ray food inspection station, comprising:

a console enclosure containing the electronic circuitry in an interior region thereof;

a heat-dissipating duct, external to the console enclosure, having two ends that are both in airflow communication with the interior region of the console enclosure which is otherwise made substantially airtight, thus forming a closed loop air passageway that includes said duct and the console enclosure, said duct being made from metal in tubular form, configured in a U-shape with both upwardly-extending legs connected to a bottom panel of the console enclosure at respective through-openings, and being made and arranged to also contribute substantially to structural support of the control console;

a first electric fan located near a first end region of said heat-dissipating duct, made and arranged to promote circulation of air around the closed loop air passageway;

a base platform, made and arranged to provide ground-level support of the console enclosure, attached in a supportive manner to said heat-dissipating duct in a lower region thereof; and a straight support strut configured as a metal tube attached to the base platform and the bottom panel of the console enclosure, and extending there-between in a predominantly vertical inclined direction.

2. The combined support structure and cooling duct system as defined in claim 1 wherein said straight support strut is made and arranged to serve as a conduit for an interconnecting cable associated with the electronic circuitry.

3. The combined support structure and cooling duct system as defined in claim 1 further comprising a second electric fan located near a second end region of said heat-dissipating duct, made and arranged to further promote circulation of air around the closed loop air passageway.

* * * * *